United States Patent [19]

Anderson

[11] Patent Number: 5,058,575
[45] Date of Patent: Oct. 22, 1991

[54] SPLINT DEVICE

[75] Inventor: John P. Anderson, Norco, Calif.

[73] Assignee: Hartwell Medical Corporation, San Marcos, Calif.

[21] Appl. No.: 637,642

[22] Filed: Jan. 4, 1991

[51] Int. Cl.⁵ ............................ A61F 5/04; A61F 5/37; A61G 1/00

[52] U.S. Cl. .................................. 128/87 R; 128/875; 5/82 R

[58] Field of Search ...................... 128/87 B, 85, 87 R, 128/75, 76 R, 87 S, 78, 83, 85, 87 A, 88, 89 R, 870; 5/82 R

[56] References Cited

U.S. PATENT DOCUMENTS

| | | | |
|---|---|---|---|
| 2,489,828 | 11/1949 | Springer | 5/82 R |
| 3,158,875 | 1/1964 | Fletcher | 5/82 R |
| 3,620,211 | 11/1971 | Goodell | 128/78 |
| 4,211,218 | 6/1980 | Kendrick | 128/870 |
| 4,280,490 | 7/1981 | Santy | 128/88 |
| 4,422,454 | 12/1983 | English | 5/82 R |
| 4,506,664 | 3/1985 | Brault | 5/82 R |
| 4,593,788 | 6/1986 | Miller | 128/87 R |
| 4,594,999 | 6/1986 | Nesbitt | 128/869 |
| 4,601,075 | 7/1986 | Smith | 5/82 R |
| 4,718,412 | 1/1988 | Nesbitt | 128/874 |
| 4,776,327 | 10/1988 | Russell | 128/875 |
| 4,911,150 | 3/1990 | Farley | 128/87 R |
| 4,936,296 | 6/1990 | Russell | 128/875 |
| 4,979,520 | 12/1990 | Boone, Jr. | 128/870 |

Primary Examiner—Danton D. DeMille
Assistant Examiner—Michael Brown
Attorney, Agent, or Firm—Harris, Kern, Wallen & Tinsley

[57] ABSTRACT

A splint device for immobilizing the spine of a patient, including a frame having a central support, first wings for fixing the head of the patient to the central support, second wings for fixing the trunk of the patient to the central support, and attachments for joining the respective wings together about the patient, an open central channel and right and left channels on each side of and parallel to the central channel in the frame central support, a cover fixed to the frame and overlying the central support enclosing the channels, each of the right and left channels having an open end, and with stiffener bars slidably insertable into the enclosed right and left channels through the open ends thereof.

9 Claims, 5 Drawing Sheets

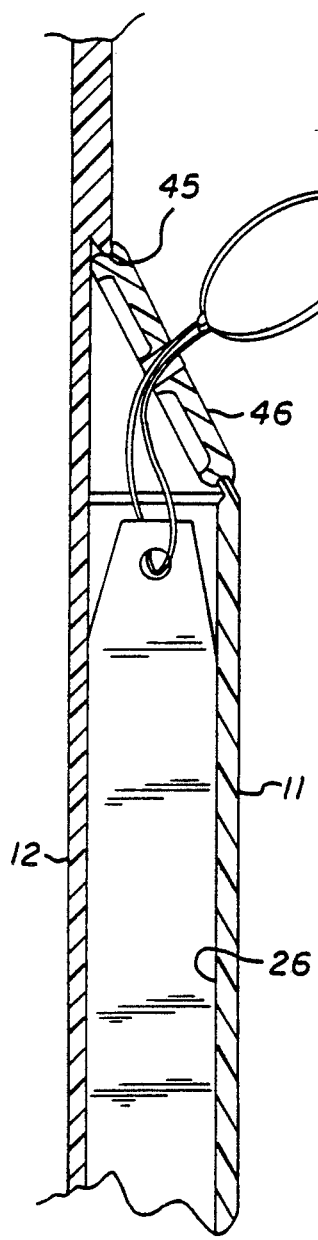
FIG. 6
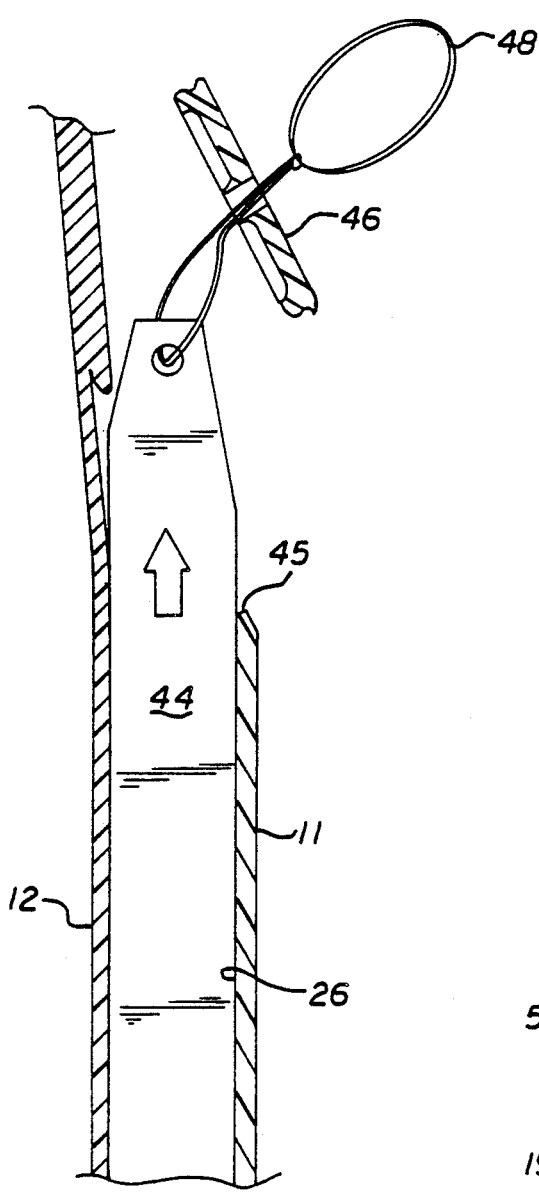
FIG. 5
FIG. 7
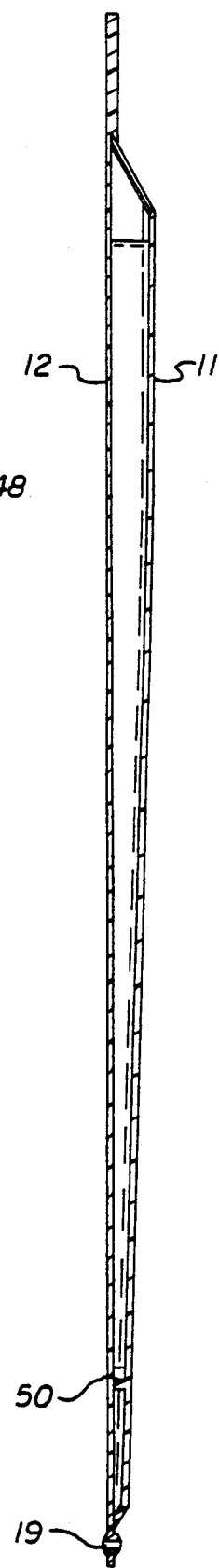

SPLINT DEVICE

BACKGROUND OF THE INVENTION

The present invention relates to a splint device for immobilizing the spine of a patient. Splint devices of this type are widely used today, particularly in the handling of patients for removal from motor vehicle accidents, building construction accidents and the like, and subsequent transportation of the patient to a medical facility for diagnosis. The purpose of the splint device is to provide a piece of equipment which is easily attached to the patient with a minimum of movement of the patient, which then provides for movement of the patient and the device as a single unit so that the spinal column of the patient is not placed under stress during removal and transportation.

One such prior art device is shown in the Kendrick U.S. Pat. No. 4,211,218. This device uses a number of strips of wood mounted in a flexible fabric body member, with the wood pieces serving as battens for stiffening purposes. Another prior art device is shown in the Russell U.S. Pat. No. 4,776,327. The Russell device is formed of a molded plastic frame with wings for wrapping around the patient and an open center with a crisscross pattern of stiffeners, and a cover to form a substantially rigid center support for the patient's head and trunk.

As emergency treatment equipment and procedures continue to improve, it is now desirable to place the accident victim in a substantially rigid spint, remove the victim from the site of the accident, transport the victim to a medical facility, and move the victim to an X-Ray or MRI table for diagnosis, while maintaining the victim in the splint device. One serious problem has been encountered in this procedure utilizing the conventional splint devices such as those described above. The wooden battens and the criss-cross reinforcing members, while functioning to make the splint device substantially rigid, also introduce ambiguous patterns and shadows in the X-Ray and MRI images making location and diagnosis of spinal injury difficult and ambiguous. Metal construction of any type interferes with X-Ray images.

It is the object of the present invention to provide a new and improved splint device which will have the substantially rigid mechanical strength of existing splint devices while at the same time doing away with the diagnosis problems resulting from the prior art constructions which have provided the rigid characteristic.

It is a particular object of the invention to provide such a splint device which has the desired rigidity while having no X-Ray or MRI pattern forming characteristic along the patients spinal column. Another object is to provide such a splint device which also has an easy-to-clean, flat surface with no traps for contamination by body fluids thereby protecting against infections of all kinds.

In order to obtain the desired rigidity, the central portion of the conventional splint usually is made relatively thick, and its construction sometimes causes a problem when the patient is laid out on a table or other flat surface. There is a transition between the upper surface of the splint device and the upper surface of the table at the lower end of the splint device, which may be in the order of ¾" to 1" high. This transition can produce an undesired bend at the lower end of the patient's trunk.

It is a further object of the present invention to provide a new and improved splint device which has the desired rigidity and desired open construction along the spinal column while also substantially eliminating the stepwise change at the lower end of the splint device.

These and other objects, advantages, features and results will more fully appear in the course of the following description.

SUMMARY OF THE INVENTION

A splint device for immobilizing the spine of a patient and including a frame, a cover, and stiffener bars. The frame has a central support with wing means for fixing about the head of the patient and about the trunk of the patient for holding the patient in the splint device. The frame has a central support with an open central channel and right and left channels on each side of and parallel to the central channel, with the cover fixed to the frame and overlying the central support enclosing the channels. The stiffener bars are slidably insertable into the enclosed right and left channels to provide the desired overall rigidity while avoiding having any X-Ray and/or MRI image distortion producing elements along the spinal column of the patient.

In the preferred environment, the frame is formed with the channels tapering in depth from the top to the bottom and with the stiffener bars having a corresponding taper so as to obtain the desired minimal thickness of the lower end of the splint. Also, the stiffener bars preferrably are formed by pultrusion in order to achieve the desired rigidity with a minimum of thickness and weight while avoiding the usage of metal members.

BRIEF DESCRIPTION OF THE DRAWINGS

FIG. 5 is a side view, partly in section, of the frame of FIG. 2, showing the cover in place;

FIG. 6 is an enlarged partial side sectional view illustrating the positioning of a stiffener bar in the splint device;

FIG. 7 is a view similar to that of FIG. 6 illustrating the removal of a stiffener bar;

DESCRIPTION OF THE PREFERRED EMBODIMENT

Figure 1:
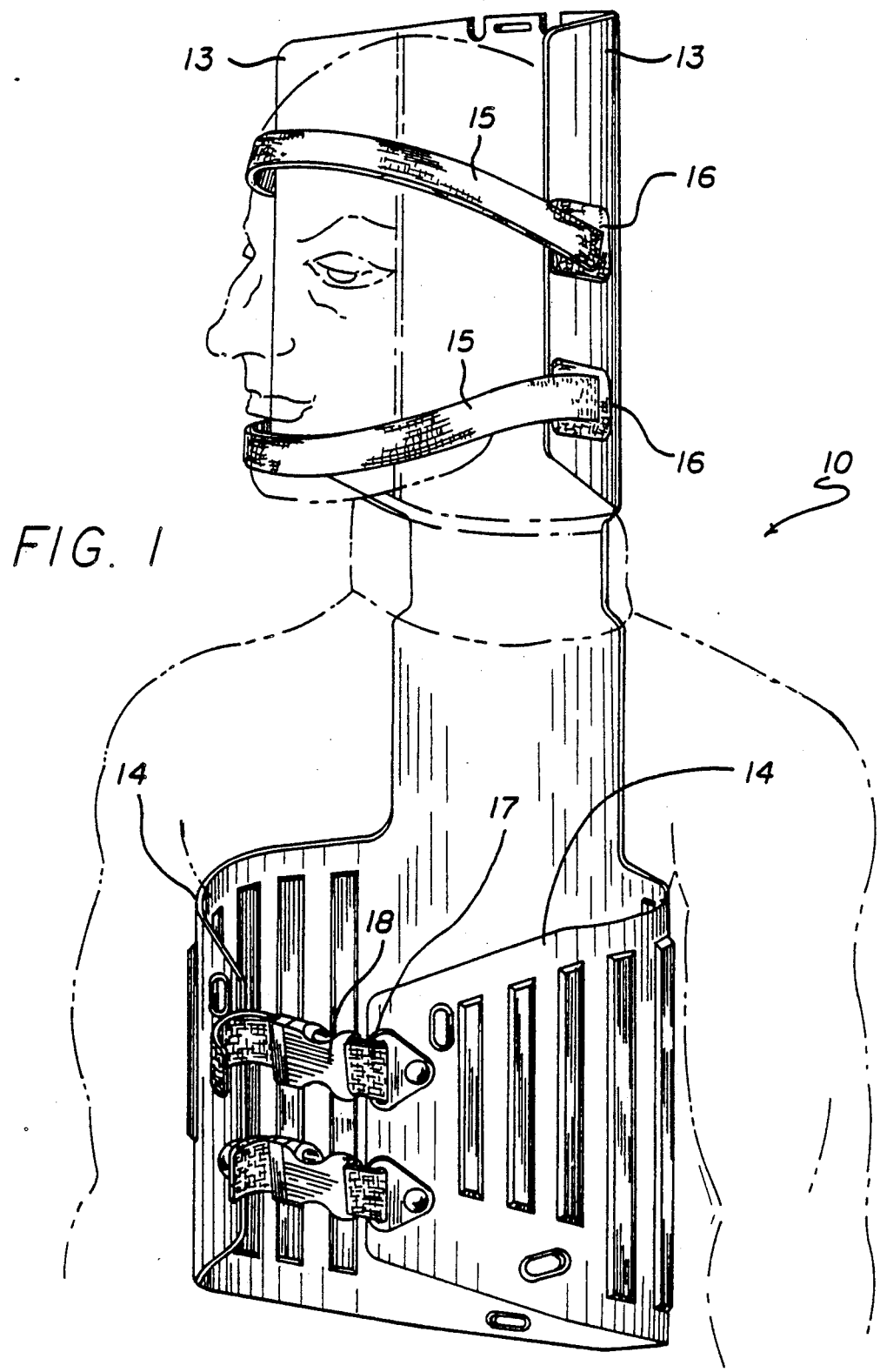
FIG. 1 is a perspective view of the presently preferred embodiment of the splint device illustrated in position on a human figure shown in phantom lines.
Figure 2:
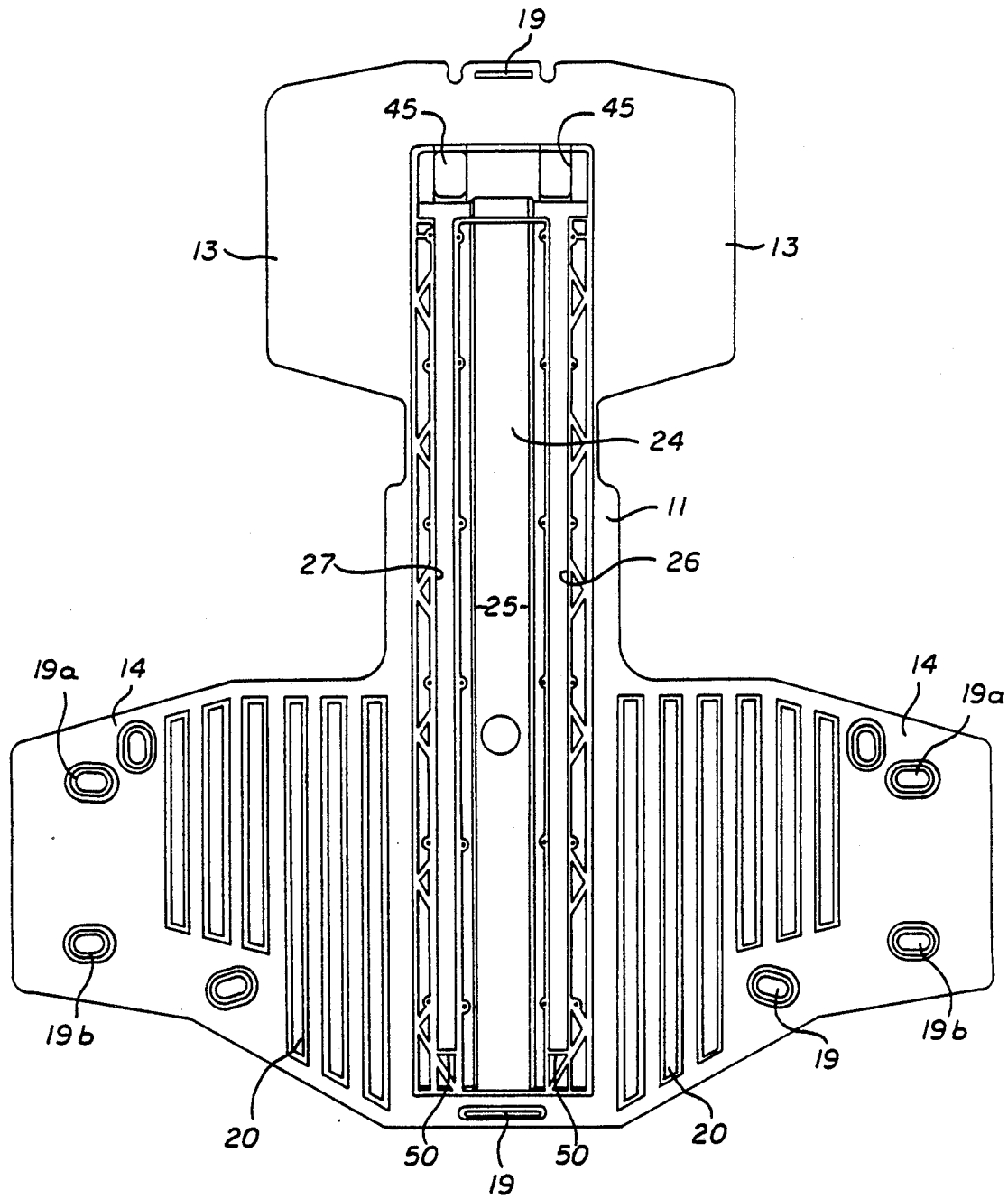
FIG. 2 is a top plan view of the frame of the splint device of FIG. 1.
Figure 3:
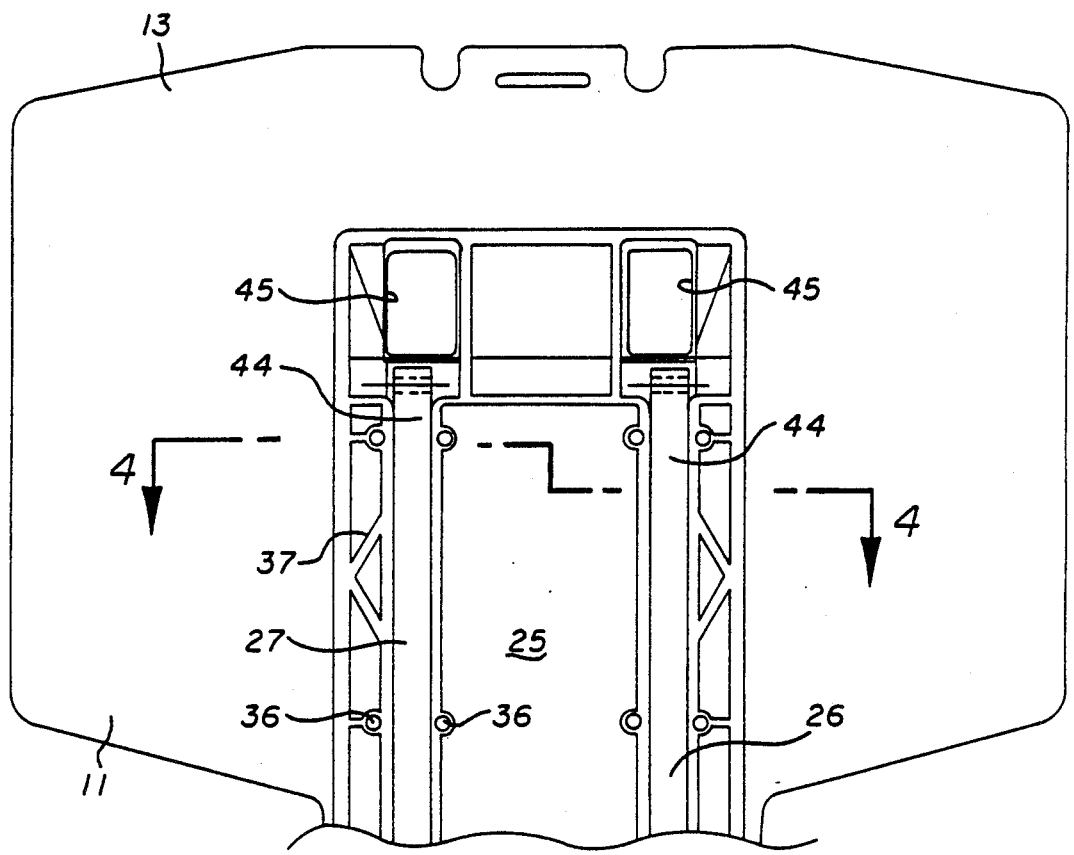
FIG. 3 is a partial enlarged view of the head end of the frame of FIG. 2.

The splint device 10 as shown in the drawings includes a frame 11 and a cover 12. The frame and cover generally may be similar to the frame and cover of the aforementioned Russell U.S. Pat. No. 4,776,327. Wings 13 are provided on the frame for positioning around the head of the patient and wings 14 are provided on the frame for positioning around the trunk of the patient, in the manner shown in FIG. 1. The opposing wings 13 typically are connected by straps 15 which are attached to the wings by hook and loop fasteners 16, which fasteners are sometimes known as Velcro fasteners. The wings 14 typically are connected by straps 17 with quick connect and disconnect buckles 18. A variety of openings 19 are provided for attachment of straps and parallel corrugations 20 are provided for flexibility in wrapping the wings about the patient while also providing increased stiffness along the vertical axis of the splint. The construction described thus far is conventional.

The wings of the frame project on opposite sides of a central support 24, the construction of which is new and a feature of the present invention. The central support includes a central channel 25, a right channel 26, and a left channel 27, with the right and left channels parallel to the central channel. The preferred embodiment also includes outer channels 28 and 29 parallel to the channels 25, 26 and 27. Typically the outer walls 30 of the outer channels slope upward to form a top plane 31 with the wings, and define a ledge 32 for receiving the cover 12 so that the top surface of the splint device on which the patient rests is substantially planar.

Figure 4:
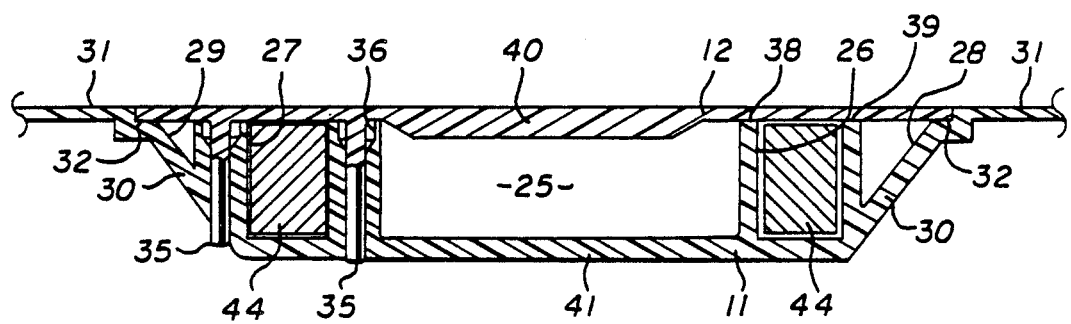
FIG. 4 is an enlarged partial sectional view taken along the line 4—4 of FIG. 3.

In the preferred embodiment, both the frame and the cover are plastic moldings with studs 35 formed integral with the top 12 and positioned for entering stud openings 36 in the frame 11. The cover may be fixed to the frame by heat and pressure sealing at the ends of the studs and if desired by cementing at the periphery of the cover and the ledge 32. A criss-cross rib pattern 37 may be provided in the outer channels 28, 29 for additional stiffening if desired. Also, the cover may be bonded to the top edges of the walls which form the channels, such as at the edges 38 and 39 in FIG. 4, for additional rigidity. An adhesive can be used for the bonding. An alternate and commonly used method for attaching the cover at the periphery and along the top edges of the channel walls is to use ultrasonic or vibration welding. The friction created by the ultrasonic waves or vibration between the two pieces of plastic, the frame and the cover, generates heat that causes localized melting of the plastic surfaces that are in contact, and they become fused together. This method of bonding is useful when a grade of plastic is used that does not readily lend itself to adhesive bonding.

The joinder of the cover to the walls which form the channels produces, in effect, box beams which have substantial rigidity without requiring internal bracing. If desired, the cover 12 may have a central section of platform 40 of increased thickness, and the frame 11 may have a similar section or platform 41 of increased thickness at the central channel 25, which construction provides enhanced rigidity without introducing shadow and/or distortion forming structures along the patient's spinal column.

Stiffener bars 44 are positioned in the right and left channels 26, 27. These stiffener bars are slidably insertable into the channels and removable from the channels. With this arrangement, the splint device will have less rigidity when the bars are removed. This permits some flexing of the splint device if required while being placed on the patient, with the bars being inserted after the patient is strapped in with the wings. Also, this construction permits removal of these bars after the patient is on the X-Ray or MRI table if desired, to reduce potential problems with the imaging and diagnosis. The use of the stiffener bars permits construction of a splint device which has a rigidity matching or exceeding that of earlier designs, while not having any pattern or shadow producing structures along the patient's spinal column. Openings 45 are provided at the upper end of the channels for passage of the stiffener bars therethrough. Preferably, these openings are closed by grommets 46, with a pull line 47 through an opening in the stiffener bar and an opening in the grommet and terminating in a finger loop 48 for pulling the bar out of the frame.

The stiffener bars may have various constructions, and could even be a solid or hollow metal bar. However, the presently preferred construction is a bar of layered reinforced plastic produced by a pulling extrusion process sometimes referred to as a pultrusion bar.

In the preferred embodiment, the depth of the channels in the frame tapers from the top to the bottom, as best seen in FIG. 5. With this construction, the overall thickness of the splint device tapers from the portion adjacent the head of the patient to the bottom end adjacent the lower end of the spine of the patient, so that there is no significant transition in support surface for the patient when the patient is in the splint device with the splint device resting on a table. With this configuration, the stiffener bars have a similar taper. The lower end of the right and left channels may be closed by a transverse wall 50 to serve as a stop for insertion of the stiffener bars.

Figure 8:
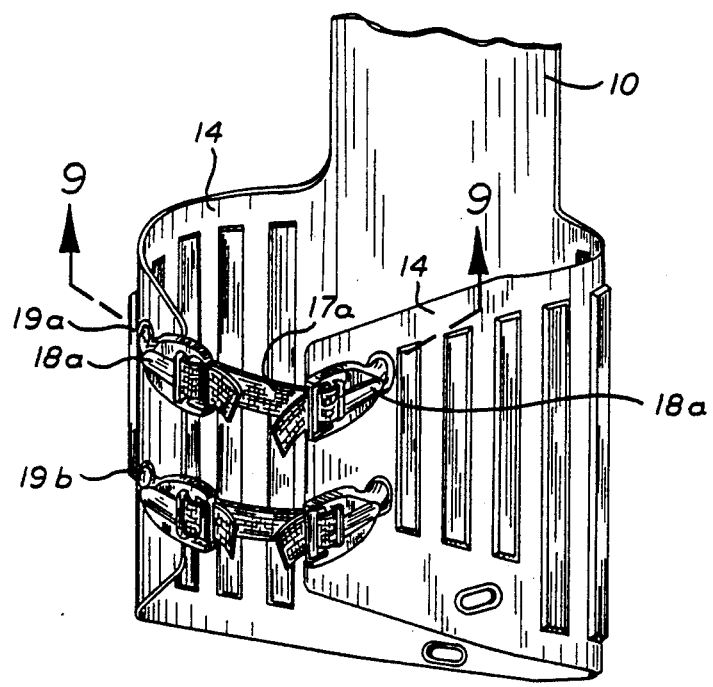
FIG. 8 is a partial view similar to that of FIG. 1, showing an alternative and presently preferred construction for the chest straps.
Figure 9:
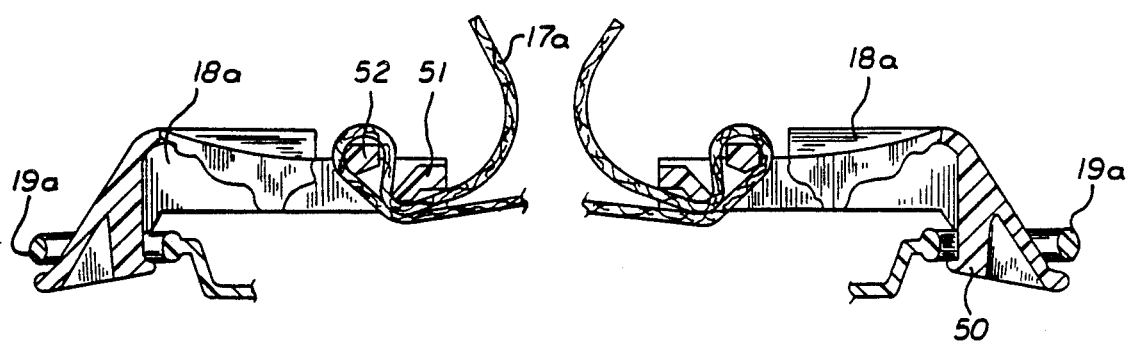
FIG. 9 is an enlarged partial sectional view taken along the line 9—9 of FIG. 8.

The presently preferred embodiment for the chest straps is shown FIGS. 8 and 9, and comprises a strap 17a and two strap terminals 18a. Typically the terminals are of a molded plastic with an enlarged oval end of a shape to pass through an opening 19a when turned at one alignment, and to be held within the opening 19a when turned 90 degrees to that alignment, as shown in FIG. 9. A strap 17a is looped around transverse bars 51, 52 in each terminal.

With this configuration, the strap and terminals can be completely removed from the frame to facilitate installation onto a patient and to simplify cleaning or replacement of the straps. In use, the terminals can be installed individually after which the strap is looped through the terminals and pulled tight. Alternatively, the strap may be inserted in the terminals first, after which the terminals are inserted into the terminal openings.

I claim:

1. In a splint device for immobilizing the spine of a patient, the combination of:
 a frame having a central support, first wing means for fixing the head of the patient to the central support, second wing means for fixing teh trunk of the patient to the central support, and attachment means for joining the respective wing means together about the patient,
 said frame central support including means defining an open central channel and right and left channels on each side of and parallel to said central channel;
 a cover fixed to said frame and overlying said central support enclosing said channels, with each of said right and left channels having an open end; and
 stiffener bars slidably insertable into said enclosed right and left channels through said open ends thereof.

2. A splint device as defined in claim 1 including outer channels respectively outside said right and left channels and enclosed by said cover, with each of said outer channels having stiffener ribs between the walls thereof.

3. A splint device as defined in claim 1 wherein said frame central support includes a recessed ledge about said channels, with said cover mounted on said ledge and providing a smooth upper surface for said frame.

4. A splint device as defined in claim 3 including a plurality of studs carried on said cover and a corresponding plurality of stud openings in said frame, which said studs fixed in said openings for joining said cover to said frame.

5. A splint device as defined in claim 4 including a frame platform in said open central channel and a cover platform on said cover, with said platforms facing each other in said central channel.

6. A splint device as defined in claim 1 with said right and left channel open ends adjacent said first wing means, and
   wherein said channels taper in depth from a greater thickness at said open ends to a lesser thickness at the opposite end of said splint device.

7. A splint device as defined in claim 6 wherein said stiffener bars are layered reinforced plastic pultrusion bars with a taper corresponding to that of said right and left channels.

8. A splint device as defined in claim 1 wherein said stiffener bars are layered reinforced plastic pultrusion bars.

9. A splint device is defined in claim 1 wherein said attachment means includes:
   strap;
   means defining a strap opening in each of said second wing means; and
   a pair of strap terminals, with each terminal having means for adjustably receiving a portion of said strap, and each having a terminal boss for insertion into one of said strap openings;
   with said terminal bosses and said strap openings being non-round so that a terminal boss will pass through a strap opening when at one orientation and not pass through when at another orientation oblique to said one orientation.

* * * * *